US008797395B2

(12) United States Patent
Harding et al.

(10) Patent No.: US 8,797,395 B2
(45) Date of Patent: Aug. 5, 2014

(54) OPTICAL SYSTEM FOR INSPECTING POROUS SUBSTRATES

(75) Inventors: Kevin George Harding, Niskayuna, NY (US); Yana Zhang Williams, Schenectady, NY (US); Esmaeil Heidari, Guilderland, NY (US)

(73) Assignee: General Electric Company, Niskayuna, NY (US)

( * ) Notice: Subject to any disclaimer, the term of this patent is extended or adjusted under 35 U.S.C. 154(b) by 632 days.

(21) Appl. No.: 12/972,167

(22) Filed: Dec. 17, 2010

(65) Prior Publication Data

US 2012/0154560 A1    Jun. 21, 2012

(51) Int. Cl.
  *G02B 21/00* (2006.01)
  *G01N 21/84* (2006.01)
  *G02B 21/36* (2006.01)

(52) U.S. Cl.
  CPC ........ *G01N 21/84* (2013.01); *G01N 2021/8444* (2013.01); *G02B 21/365* (2013.01)
  USPC .......................................................... 348/79

(58) Field of Classification Search
  CPC .................................................. G02B 21/365
  See application file for complete search history.

(56) References Cited

U.S. PATENT DOCUMENTS

2005/0271421 A1* 12/2005 Uemura et al. ............... 399/191
2009/0176271 A1*  7/2009 Durack et al. ............... 435/40.5
2009/0231689 A1*  9/2009 Pittsyn et al. ................. 359/363

FOREIGN PATENT DOCUMENTS

JP          2008232664 A    10/2008

OTHER PUBLICATIONS

Starov et al. "Spreading of Liquid Drops over Dry Porous Layers: Complete Wetting Case", Journal of Colloidal and Interface Science, vol. 252, p. 397-408.*

* cited by examiner

*Primary Examiner* — Sath V Perungavoor
*Assistant Examiner* — Kate Luo
(74) *Attorney, Agent, or Firm* — Jenifer E. Haeckl

(57) ABSTRACT

An automated system for inspecting a porous substrate using a sample, comprising, a delivery device positioned to apply the sample to a target point on the porous substrate along a sample axis; an imaging device and one or more lenses, positioned so that the imaging device and the lens each has a focus axis that is offset from the sample axis, and have a viewing focal point that is substantially the same as the target point; a light source that is offset from the delivery device to illuminate the surface target; and a processor comprising a data acquisition and control system that coordinates timing and automation of the delivery and imaging devices, and determines one or more characteristics of the porous substrate.

21 Claims, 9 Drawing Sheets

OPTICAL SYSTEM FOR INSPECTING POROUS SUBSTRATES

BACKGROUND

The invention relates generally to systems for inspecting porous substrates.

Porous substrates, such as cellulose and cotton matrices (e.g. 31 ETF, FTA and FTA elute cards available from Whatman) are often used to store biological samples, such as blood. In addition to forensic uses, a new application area for these cards is in the pharmaceutical industry, which is using them to store dried blood samples from pharmacokinetic and toxicokinetic studies. Sensitivity, accuracy and consistency has become even more important. To achieve the necessary quality requirements for these applications, the quality and consistency of the porous substrate is essential.

The porous substrate material is typically manufactured in rolls and then cut into pieces. As shown in FIG. 1, currently, the quality of the paper is checked by a person who manually drops a sample liquid onto the paper with a pipette and then manually quantifies the rate at which the liquid was absorbed by the paper. The measurements used to quantify the rate of absorption are taken by a person who manually measures a given spot of liquid with calipers multiple times over a period of time as the spot expands. This method is slow, tedious and subject to error throughout the manual process of spotting the paper, measuring the spot with calipers over time using a stopwatch as it expands and then calculating the rate of expansion based on the measurements over time. The rate of expansion is typically calculated manually by a technician and then entered into a log, or the measurement data is manually entered into a system and calculated by the system.

As such, there exists a need for an automated method and system for inspecting porous substrates during the manufacturing process. More specifically, there is a need for methods and systems that are able to consistently quantify the characteristics and quality of porous substrates.

BRIEF DESCRIPTION

One embodiment of the automated system of the invention, for inspecting a porous substrate using a sample generally comprises: a delivery device positioned to apply a sample, such as a blood or other liquid sample, to a target point on the porous substrate along a sample axis; an imaging device and one or more lenses, positioned so that the imaging device and the lens each has a focus axis, that is offset from the sample axis, and having a viewing focal point that is substantially the same as the target point; a light source that is offset from the delivery device to illuminate the substrate and the surface target; and a processor comprising a data acquisition and control system that coordinates timing and automation of the delivery and imaging devices, and determines one or more characteristics of the porous substrate. In at least one embodiment, the delivery device, illumination source, imaging device and processor are in fixed positions relative to each other.

In one or more embodiments, the delivery device is a syringe pump. The delivery device may comprise a needle having a longitudinal axis that is in-line or offset from the sample axis. However, other delivery devices, such as, but not limited to, an automated pipette or dropper, may also used.

The light source may be, but is not limited to, a light emitting diode (LED) such as a white LED or a strobe LED. The light may have a variety of shapes such as, but not limited to, ring lights, bar lights and overhead flat panel lights. In one or more of the embodiments, the imaging device is a CCD camera. In one or more embodiments, the imaging device has a focus axis that is offset from the sample axis in a range from 50 to 75 mm, and the lens has a focal axis that is offset from the focus axis of the imaging device in a range from 10 to 15 mm.

In one or more embodiments, the data acquisition and control system is configured to automatically initiate the delivery device to apply a sample to a substrate and to initiate the imaging device to acquire one or more images of the substrate in an area corresponding to the target point as the sample is absorbed by the substrate, wherein the data acquisition and control system identifies a sample spot in one or more of the images and determines one or more parameters of the sample spot over one or more time intervals. The data acquisition and control system may determine a rate of absorption based on one or more of the parameters determined over one or more time intervals. Any one of the characteristics of the porous substrate that are determined by the data acquisition and control system may be based on one or more of the parameters. One or more of the characteristics of the porous substrate may also be determined based at least in part on the rate of absorption. One or more of the characteristics of the porous substrate that are determined by the data acquisition and control system may comprise, but are not limited to, weight, thickness, density, porosity, uniformity, topology, roughness, orientation, chemical composition and curvature.

The data acquisition and control system are configured to automatically initiate the delivery device to apply a sample to a substrate, to initiate the imaging device to acquire one or more images of the substrate in an area corresponding to the target point as the sample is absorbed by the substrate, and to identify and map the sample in the images. In one or more embodiments, the data acquisition and control system is configured to identify one or more major and minor dimensions of the sample. The system may acquire one or more static measurements and one or more dynamic measurements of the sample, wherein one or more of the static measurements may comprise, but are not limited to, one or more of, major diameter, semi-major diameter, minor diameter, semi-minor diameter, spot edge regularity and total area; and wherein one or more of the dynamic measurements may comprise, but are not limited to, one or more of, rate of absorption, changes in major and minor dimensions, color intensity, grey scale intensity and reflectance.

DRAWINGS

These and other features, aspects, and advantages of the present invention will become better understood when the following detailed description is read with reference to the accompanying drawings in which like characters represent like parts throughout the drawings, wherein.

DETAILED DESCRIPTION

Figure 1:
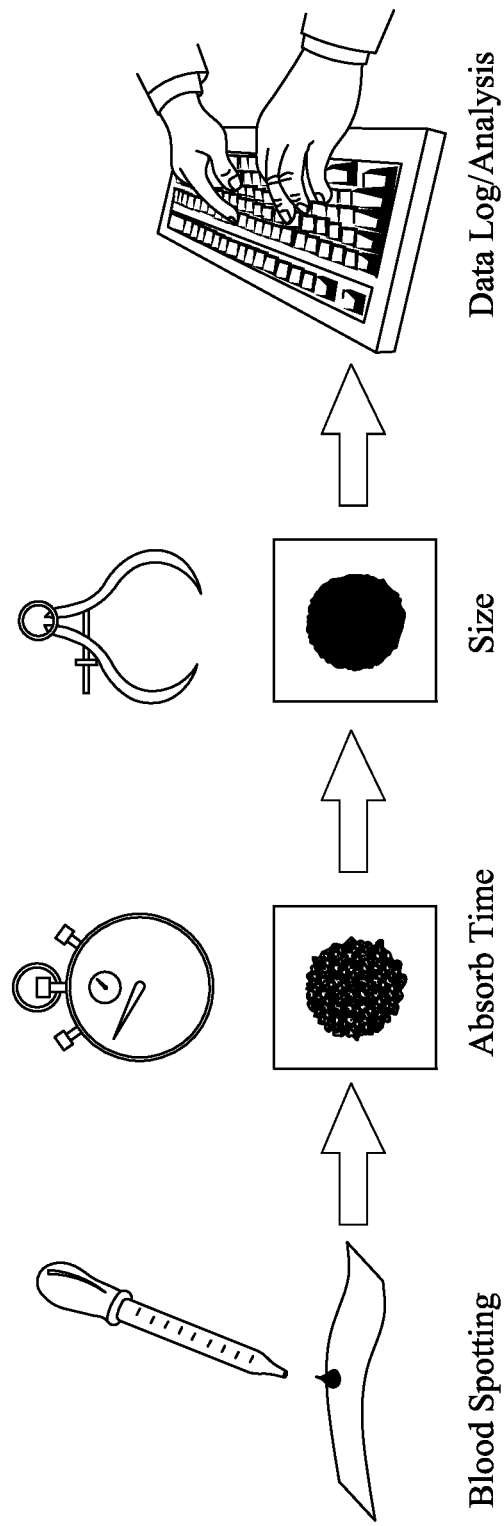
FIG. 1 is an example of typical work flow of the prior art.
Figure 2:
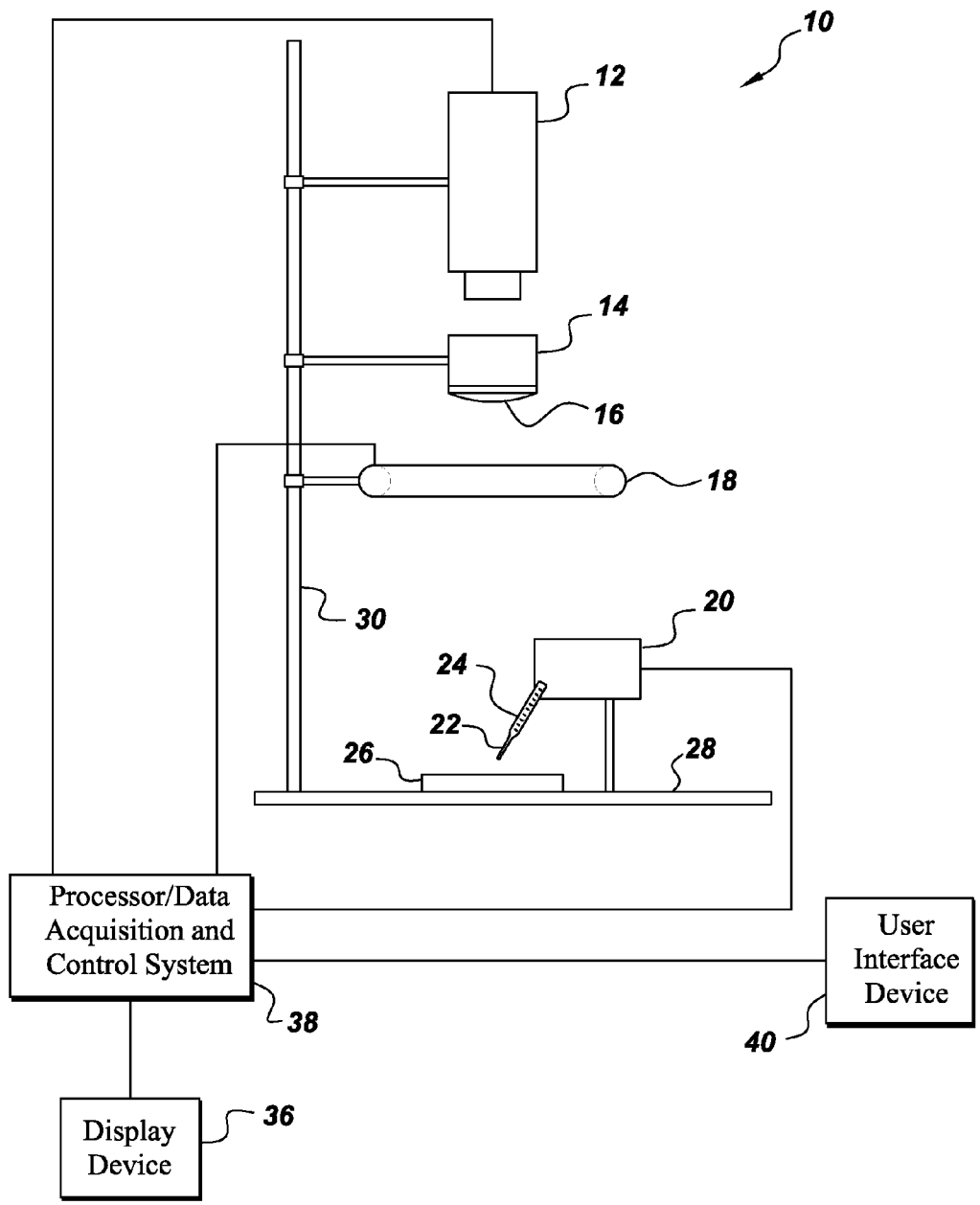
FIG. 2 is a schematic drawing of an embodiment of the system of the invention.

One embodiment of the automated system of the invention, for inspecting a porous substrate using a sample, is generally shown and referred to in FIG. 2 as system 10. System 10 generally comprises: a delivery device 20 positioned to apply a sample, such as a blood or other liquid sample, to a target point on the porous substrate 26 along a sample axis 30 (shown in FIG. 3); an imaging device 12 and one or more lenses 16, positioned with lens support 14 so that the imaging device 12 and the lens 16 each has a focus or optical axis, such as axes 33 and 35, respectively, that are offset (or otherwise referred to as translated) from the sample axis 30, and having a viewing focal point 34 that is substantially the same as the target point 36; a light source 18 that is offset from the delivery device 20 to illuminate the substrate 26 and the surface target; and a processor 36 comprising a data acquisition and control system that coordinates timing and automation of the delivery and imaging devices, and determines one or more characteristics of the porous substrate 26. Axis 32 is a viewing axis that is at an angle to the sample axis or porous substrate and is associated with viewing focal point 34. Base 28 serves to support substrate 26. The term sample axis refers to the gravitational path that a sample drop follows as it drops from the needle tip or dropper of the delivery device which, in a closed housing not subject to outside physical influences, would follow a straight, vertical path that is perpendicular or normal to a horizontally positioned substrate.

In at least one embodiment, the delivery device, illumination source, imaging device and processor are in fixed positions relative to each other. Although the various components, such as the needle, illumination source, imaging device and lenses may be configured to move and be controlled by the processor, when the imaging device and/or the needle are offset and in a fixed position, the data acquisition and analysis are more consistent and accurate. Moving components may introduce anomalies into the system.

Figure 4:
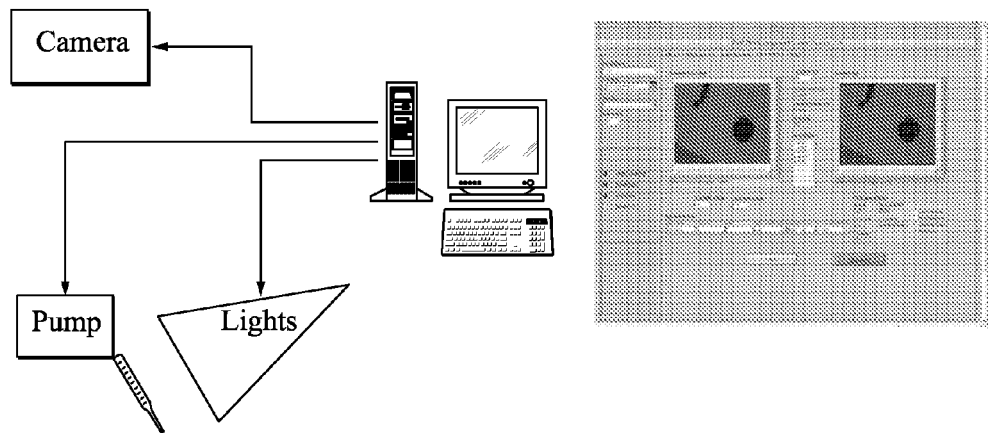
FIG. 4 is a schematic drawing of the work flow of an embodiment of the system of the invention.

System 10, including all of the components, may be contained in a single housing or one or more of the components may be standalone or peripheral devices that are connected to the system by hardwire or wirelessly. Depending on a given embodiment, either the entire housing, or a sub-housing containing the components used to capture the images, may need to be a light blocking housing to avoid interference by extraneous light or backscattering. The delivery device may also be a peripheral component to house and pump the sample or other liquid materials, such as additive chemicals or compounds, outside the system unit, whereby the materials are delivered via tubing ultimately to the syringe or needle 22 in the primary system housing. The pump of the delivery device may be housed within the primary system housing or outside, depending on the arrangement of the system. The system may comprise a display device 38 to display the images and the results of the data acquisition and analysis. As shown in FIG. 4, the system may comprise a user interaction device 40 for entering data into the system such as a keyboard or wireless device.

Figure 3:
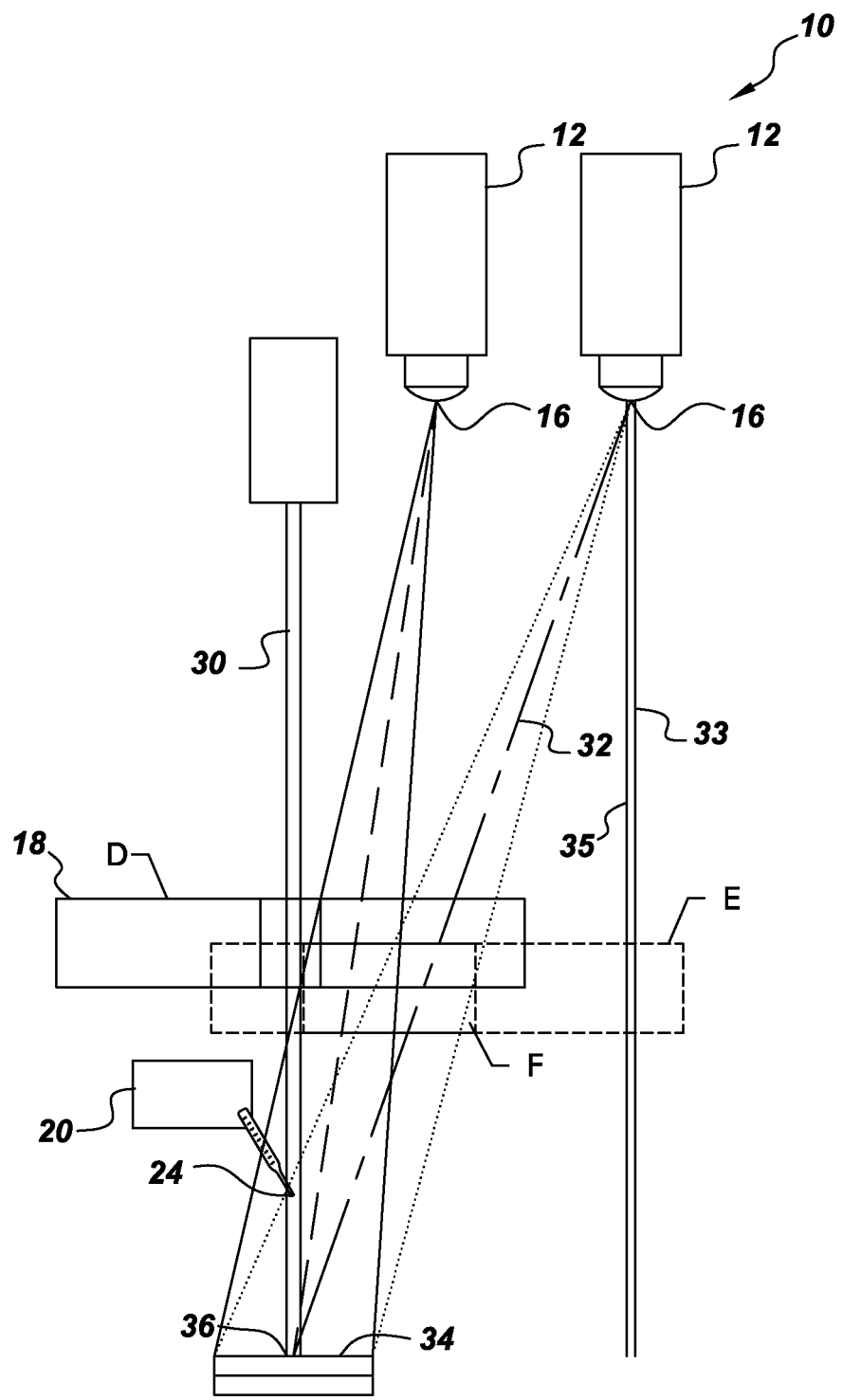
FIG. 3 is a schematic drawing of two examples of offset positions for the imaging device and a lens and two examples of positions for the delivery device, one offset and one in line with the sample axis.

In one or more embodiments, the delivery device is an automated syringe pump in liquid communication with a needle. As shown in FIG. 2 and FIG. 3, the delivery device may comprise a needle having a longitudinal axis that is in-line or offset from the sample axis. Delivery device 23 has an in-line needle that drops the sample directly from above the target point on the substrate. Delivery device 20 is offset from the target point and only needle tip 24 is positioned directly above the target point. If offset, the system may be configured so that only the distal tip 24 of the needle 22 is in, adjacent or otherwise proximate to the sample axis. Greater flexibility with the configuration of the light source, imaging device and lens is gained by offsetting the delivery device, including the needle, from the target point. Other delivery devices, such as, but not limited to, an automated pipette or dropper, may also used.

The light source may be, but is not limited to, a light emitting diode such as a white LED or a strobe LED. The light may have a variety of shapes such as, but not limited to, ring lights, bar lights and overhead flat panel lights. In one or more of the embodiments, the imaging device is a CCD camera. The speed of the camera may vary from standard speeds (e.g. 30 images per second) to higher speeds, depending on the application and the number of frames per second that are desired. The light source may also be offset as shown by positions D, E, and F in FIG. 3 to avoid vignetting in the images.

In one embodiment the lens or plurality of lenses are flat field but other types of lenses may also be used such as, but not limited to, monochromatic, portrait, corrected and large lenses. In one or more embodiments that comprise a flat field lens having a lens field angle of 45 degrees, the imaging device (camera) has a focus axis that is offset (or otherwise translated) from the sample axis in a range from about 50 to 75 mm, and the lens has an optical axis that is offset (or otherwise translated) from the camera's focus axis in a range from about 10 to 15 mm (or 40 to 60 mm off axis from the sample axis). Two examples are shown in FIG. 3. For one example, the imaging device is located at position A, in which the camera axis 33 is offset from the sample axis by about 75 mm and the lens is offset from the camera axis by about 15 mm (or 60 mm off axis from the sample axis). For the other example shown in FIG. 3, the imaging device is located at position B, in which the camera axis 35 is offset from the sample axis by about 50 mm and the lens is offset by about 10 mm from the camera axis (or 40 mm off axis from the sample axis). Other positions are possible, for example depending on the location and type of the delivery device, light source and imaging device.

Mirrors may also be incorporated into the system to vary the configuration of the system and/or to capture varying views of the blood spot.

Although the tip of the needle of the delivery device may be positioned so that the sample may be dropped from heights between, for example, 10 mm to 170 mm, it is generally better to release the sample drop from the tip of the needle closer to the substrate, for example from about 10-15 mm above the substrate, to achieve greater consistency and accuracy. At higher releases, accuracy may decline. However, the needle tip also should not be so close to the substrate as to cause the needle to interfere with the natural gravitational drop of the sample. The droplet should fall off of the tip of the needle without yet touching the substrate.

Figure 10:
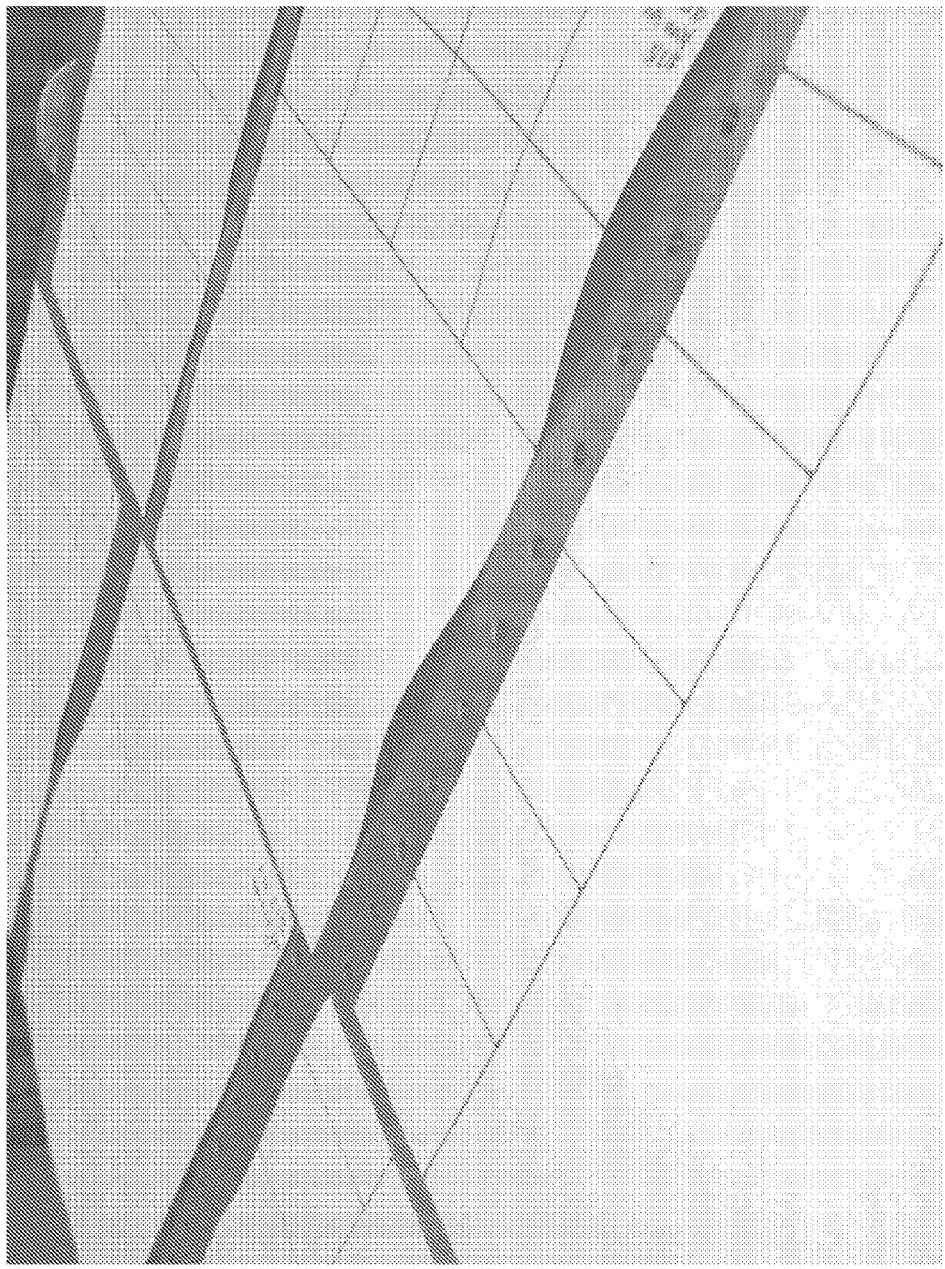
FIG. 10 is a photograph showing curling of the porous substrate material.

In one or more embodiments, the data acquisition and control system is configured to automatically initiate the delivery device to apply a sample to a substrate and to initiate the imaging device to acquire one or more images of the substrate in an area corresponding to the target point as the sample is absorbed by the substrate, wherein the data acquisition and control system identifies a sample spot in one or more of the images and determines one or more parameters of the sample spot over one or more time intervals. The data acquisition and control system may determine a rate of absorption based on one or more of the parameters determined over one or more time intervals. Any one of the characteristics of the porous substrate that are determined by the data acquisition and control system may be based at least in part on one or more of the parameters. One or more of the characteristics of the porous substrate may also be determined based at least in part on the rate of absorption. One or more of the characteristics of the porous substrate that are determined by the data acquisition and control system may comprise, but are not limited to, weight, thickness, density, porosity, uniformity, topology, roughness, orientation, chemical composition and curvature. Curvature is shown for illustration in FIG. 10.

Figure 6:
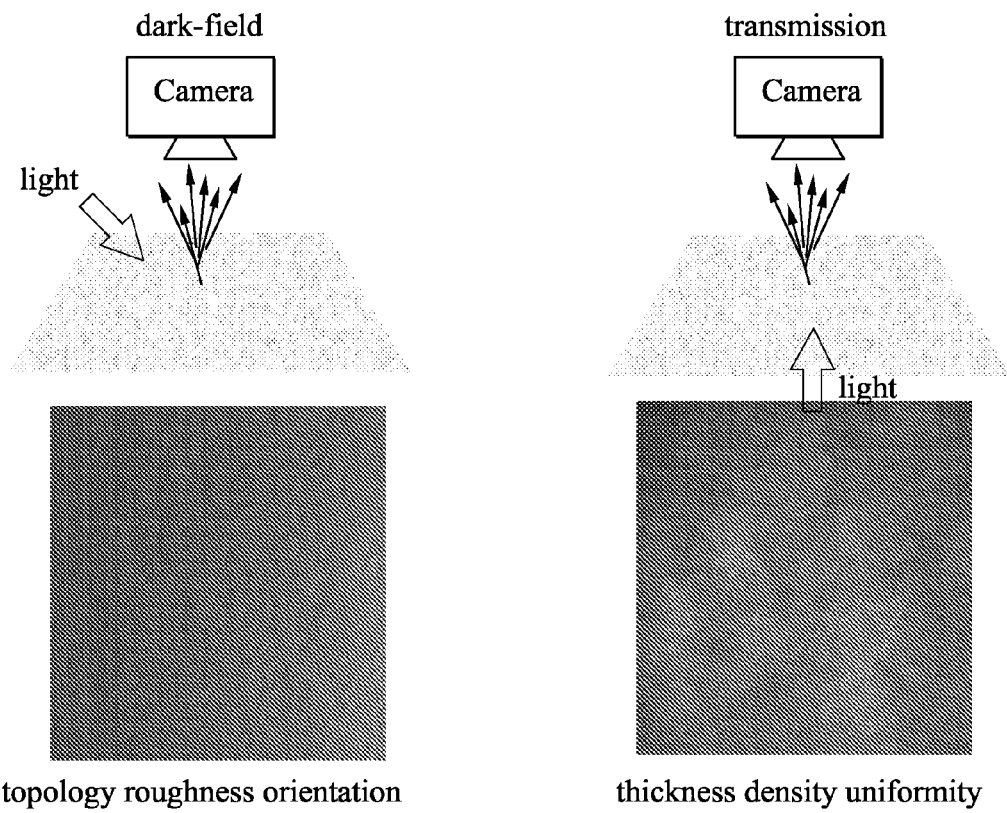
FIG. 6 show two examples of the system set up, one of which uses a dark field and reflectance and the other uses transmitted light.
Figure 7:
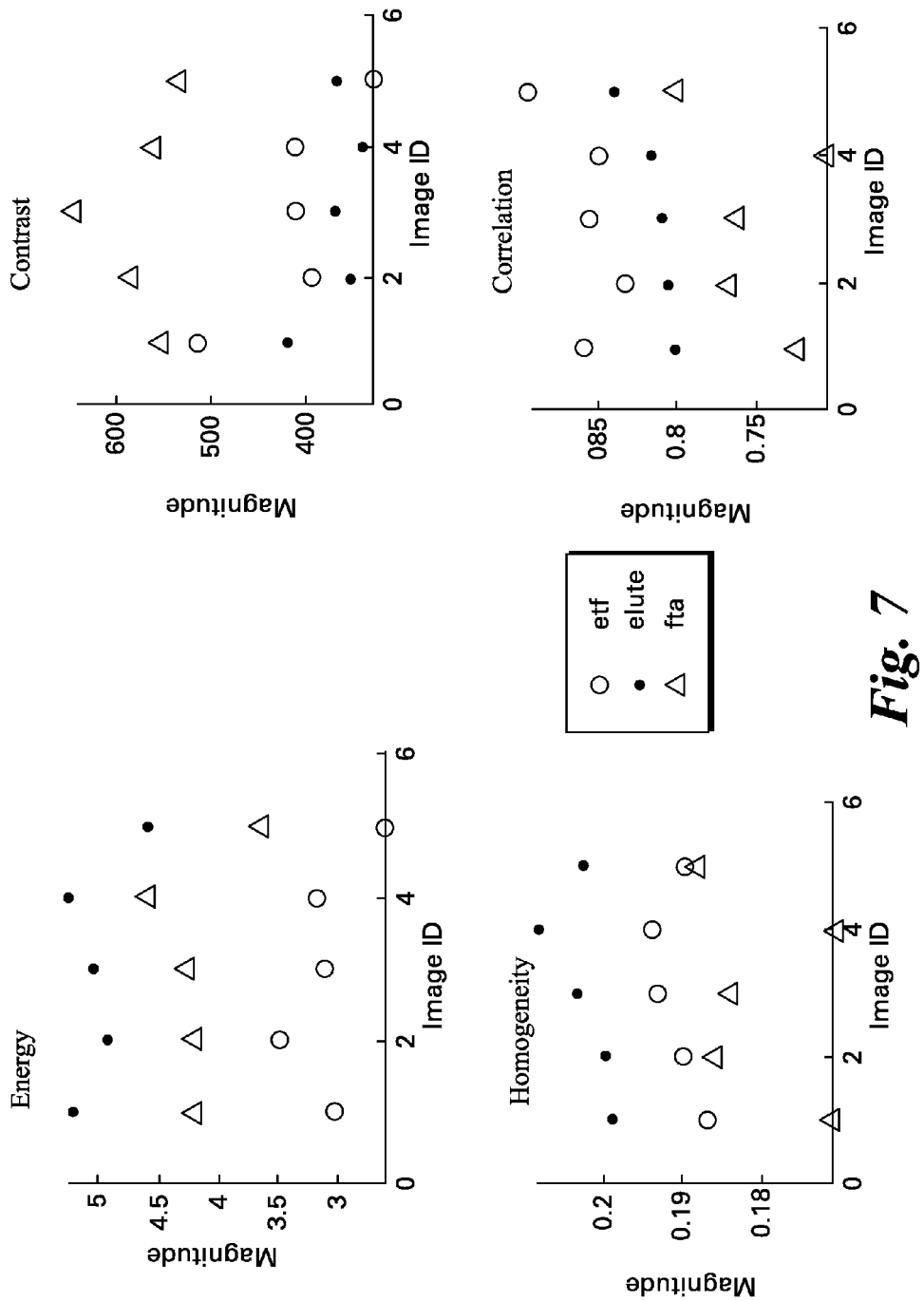
FIG. 7 show four examples of the types of data that may be analyzed using the system of the invention. The four examples are based on energy, contrast, homogeneity and correlation.

As shown in FIG. 6, characteristics, such as topology, roughness and orientation may be determined by using a dark-field and reflected light. While characteristics, such as thickness, density and uniformity may be determined using transmitted light. One optical set up is not exclusive of the other, depending on the configuration of a given system. FIG. 7 shows four examples of how the acquired data may be used to analyze the substrate. The four examples shown are energy, contrast, homogeneity and correlation.

Figure 5:
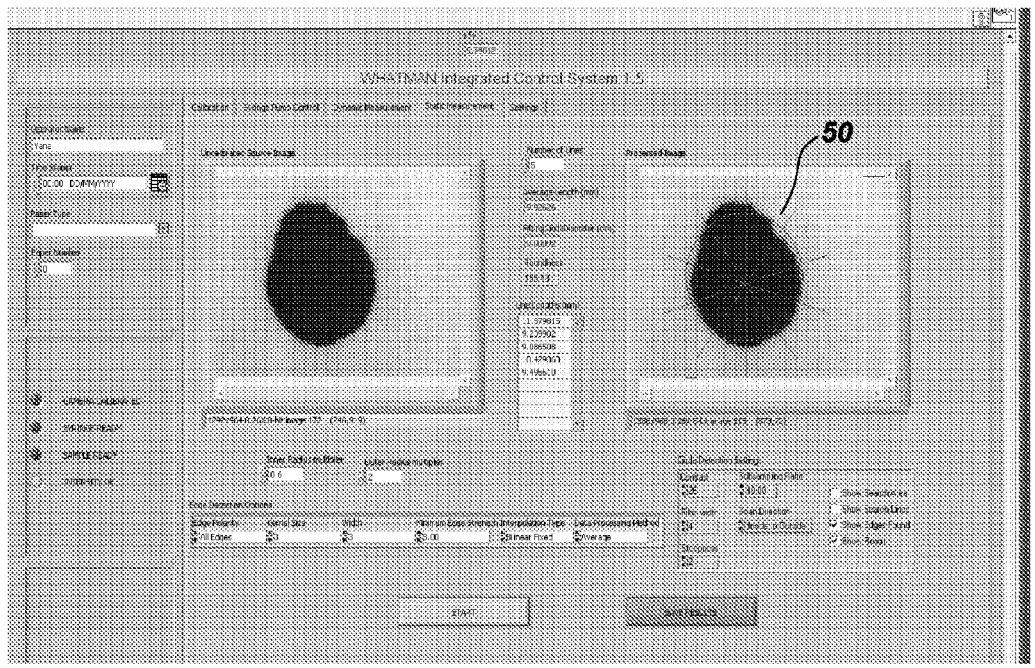
FIG. 5 is an example of a display showing an example of a map overlaid on an image.

As shown in FIG. 4, the data acquisition and control system are configured to automatically initiate the delivery device to apply a sample to a substrate, to initiate the imaging device to acquire one or more images of the substrate in an area corresponding to the target point as the sample is absorbed by the substrate, and to identify and map the sample in the images. FIG. 5 shows a display of the an uncalibrated image and a processed image 50 showing a map of the spot comprising a plurality of major and minor dimensions of the sample. The system is able to generate an image without the needle being visible in the image. The system may acquire one or more static measurements and one or more dynamic measurements of the sample. For example, the static measurements may comprise, but are not limited to, one or more of the following, major diameter, semi-major diameter, minor diameter, semi-minor diameter, spot edge regularity and total area. The dynamic measurements may comprise, but are not limited to, one or more of the following, rate of absorption, changes in major and minor dimensions, color intensity, grey scale intensity and reflectance.

Figure 8:
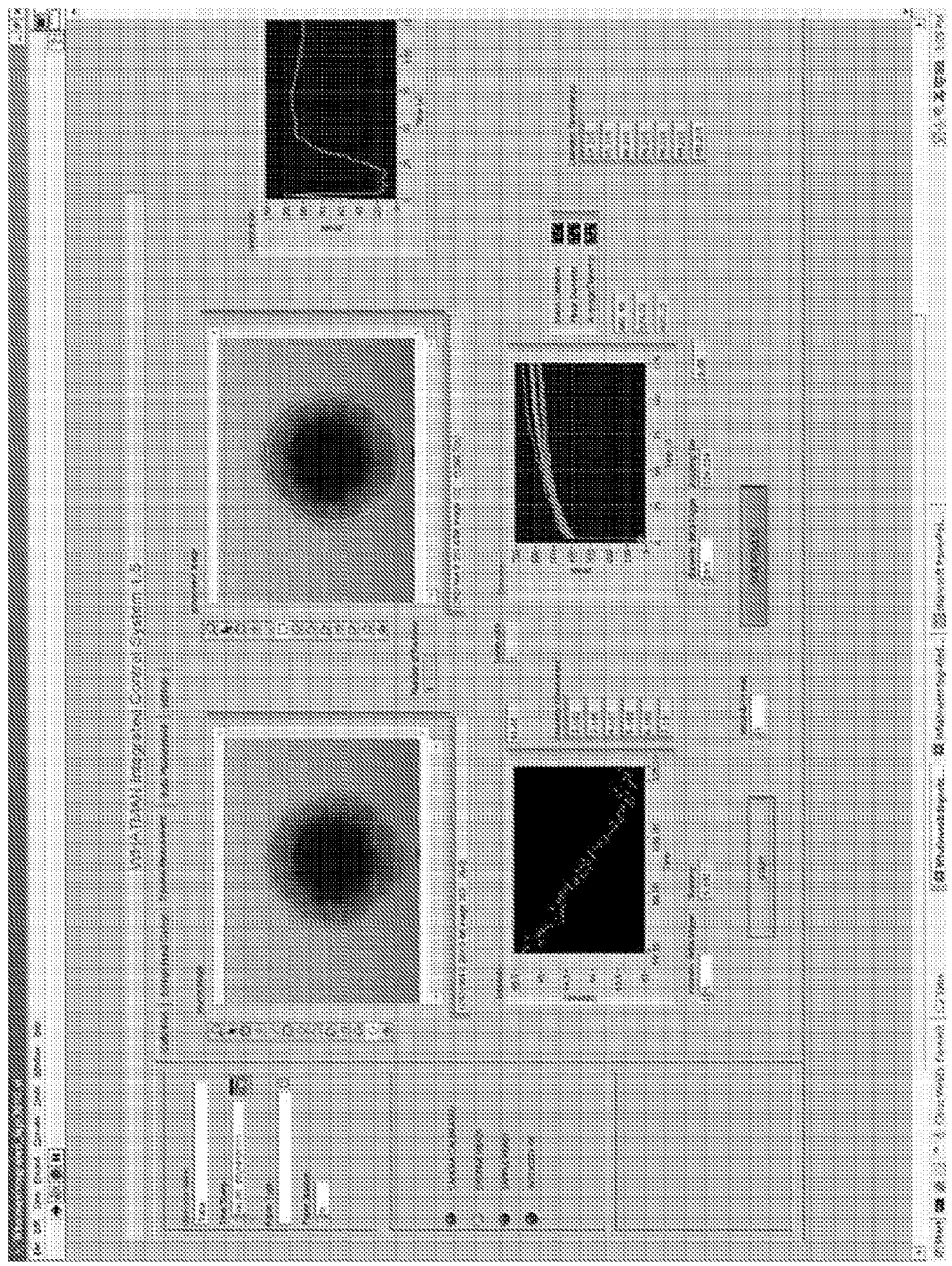
FIG. 8 is an example of a display of the images and data acquisition.
Figure 9:
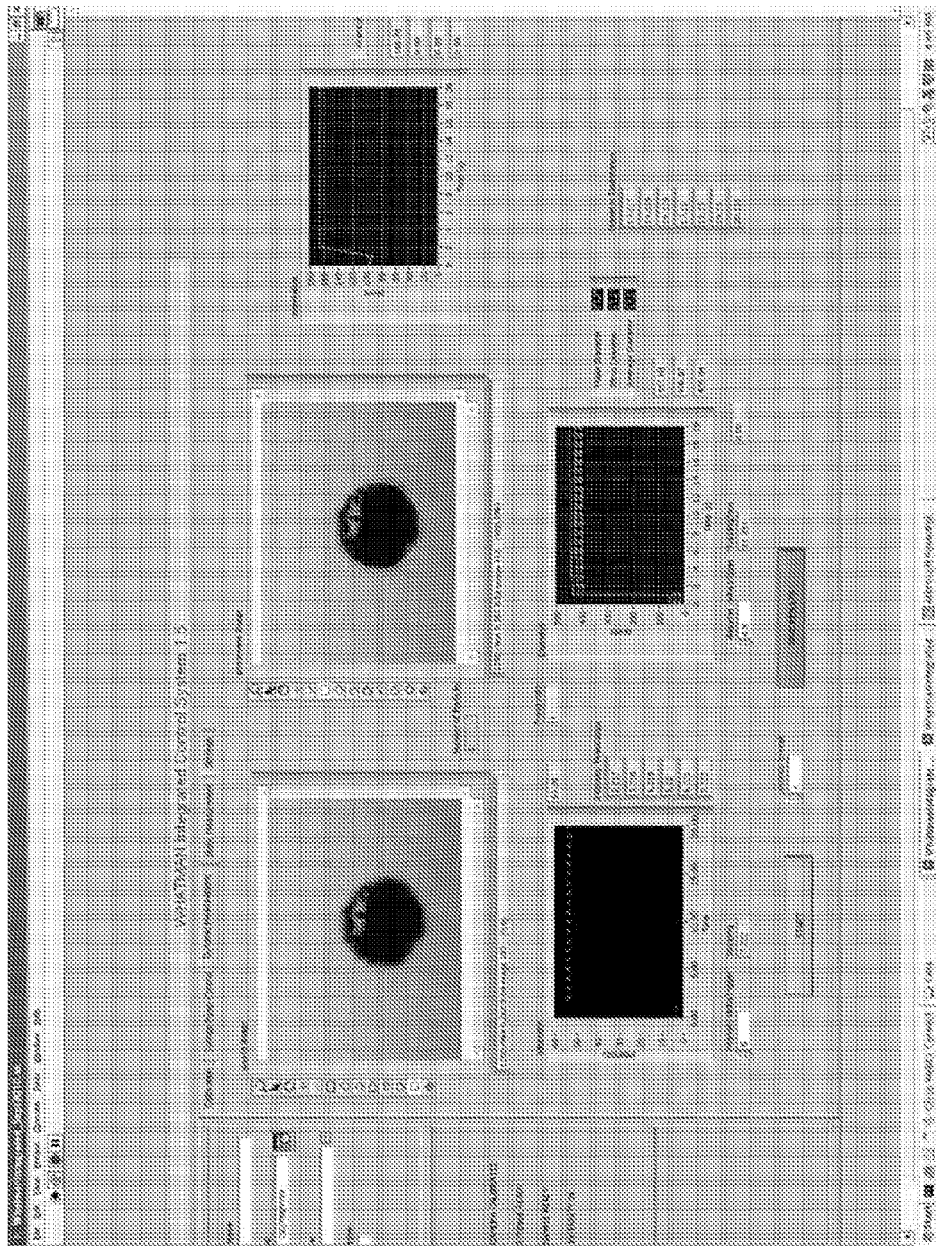
FIG. 9 is another example of a display of the images and data acquisition.

As shown in FIGS. 2 and 4, the system may comprise a display device for displaying, for example, the images and the results of the data acquisition and analysis. Two non-limiting examples of displayed images and data are shown in FIGS. 8 and 9.

The systems of the invention may be used to inspect a variety of porous substrates either in-line or off-line, during or after the manufacturing process of the paper. One application for these systems is to inspect porous substrates that are to be used in blood analysis systems that are typically used in forensics and pharmaceutical toxicology testing. The inspection and data analysis may be used for quality control or quality assurance in the paper manufacturing process and/or to feed into the analysis of the actual forensic or pharmaceutical testing.

The porous paper, typically made from cotton or cellulose, is manufactured in rolls and then cut into pieces appropriate for the analysis systems used to test blood samples. Chemical compounds that are useful in such tests may be applied during the manufacturing of the rolls of paper, applied after the rolls are cut into pieces, or applied in-line during the actual analysis of the blood spots. Since the compounds affect the properties of the porous substrate, the systems of the invention are adapted to capture and analyze the content, chemistry and concentration of such compounds that are applied to the paper as shown, for example, in the table below.

| Base Paper | Chemistry | Concentration |
|---|---|---|
| 31 ETF | none | 0 |
| 903 | FTA | 25 |
| Non-acid 31 ETF | FTA Elute | 50 |
| | | 66 |
| | | 75 |
| | | 100 |

Paper measurements may be gathered based on both transmission and reflection surface data for all types of porous substrates. This data may be stored in the processor and integrated into the algorithms of the system to be correlated later with the rate of blood-spot or sample-spot absorption during inspection. As shown in FIG. 7, various correlations are established between paper measurements and blood-spot metrics.

To test the performance of blood spot paper, such as a porous cotton substrate, the automated system drops a measured level of blood, or other sample material, onto the porous substrate. Then the system captures a plurality of serial images to measure, for example, the drop diameter over time. Software in the processor then analyzes the acquired images and data. For example, the system begins the blood spot size progression analysis starting as soon as the blood contacts the porous substrate. The results provide a detailed map of the spot size progression and spot shape without any loss of data. The automated blood spot mapping system provides repeatable and consistent data, and a digital record of the blood spot progression over time that can be used to control the quality of the paper manufacturing process and to provide additional background data that can be feed into a forensic or pharmaceutical testing system based on a given paper batch.

To obtain the best results and data on blood spot progression (absorption and spreading), the size and full shape of the spot are best tracked starting as soon as the blood first makes contact with the paper. In a short time, the blood is absorbed into the paper and then over time will continue to spread outward in the paper. The absorption time (e.g. in seconds) and the spread over time may be used as a measure of the performance of the paper for a specific type of use, e.g. blood testing. Very rapid spread or poor absorption would dilute the blood and likely make the sample unusable. The systems of the invention provide a means to continuously observing the blood spot using digital means starting immediately upon dispensing, without any areas being obscured by the delivery unit and/or imaging devices.

While only certain features of the invention have been illustrated and described herein, many modifications and changes will occur to those skilled in the art. It is, therefore, to be understood that the appended claims are intended to cover all such modifications and changes as fall within the true spirit of the invention.

The invention claimed is:

1. An automated system for inspecting a porous substrate using a sample, comprising,
   a delivery device fixed along a sample axis to apply a sample to a target point on a porous substrate, wherein the sample axis is perpendicular to the porous substrate;
   an imaging device and one or more lenses, positioned so that the imaging device and the lens each has a focus axis that is parallel but offset translationally from the sample axis, and the combination of the imaging device and the lens has a viewing focal point that is substantially the same as the target point;
   a light source that is offset from the delivery device to illuminate the surface target; and
   a processor comprising a data acquisition and control system that coordinates timing and automation of the delivery and imaging devices, and determines one or more characteristics of the porous substrate.

2. The system of claim 1, wherein the imaging device has a focus axis that is offset from the sample axis in a range from 50 to 75 mm, and the lens has a focus axis that is offset from the focus axis of the imaging device in a range from 10 to 15 mm.

3. The system of claim 1, wherein the light source is a light emitting diode.

4. The system of claim 1, wherein the light source is a ring light or a bar light.

5. The system of claim 1, wherein the delivery device is a syringe pump.

6. The system of claim 5, wherein the delivery device comprises a needle having a longitudinal axis that is offset from the sample axis.

7. The system of claim 1, wherein the imaging device is CCD camera.

8. The system of claim 1, wherein one or more of the characteristics of the porous substrate that are determined by the data acquisition and control system comprise one or more of weight, thickness, density, porosity, uniformity, topology, roughness, orientation, chemical composition and curvature.

9. The system of claim 1, wherein the data acquisition and control system is configured to automatically initiate the delivery device to apply a sample to a substrate and to initiate the imaging device to acquire one or more images of the substrate in an area corresponding to the target point as the sample is absorbed by the substrate.

10. The system of claim 9, wherein the data acquisition and control system identifies a sample spot in one or more of the images and determines one or more parameters of the sample spot over one or more time intervals.

11. The system of claim 9, wherein the data acquisition and control system determines a rate of absorption based on one or more of the parameters determined over one or more time intervals.

12. The system of claim 9, wherein one or more of the characteristics of the porous substrate that are determined by the data acquisition and control system are based on one or more of the parameters.

13. The system of claim 12, wherein one or more of the characteristics comprise one or more of weight, thickness, density, porosity, uniformity, topology, roughness, orientation, chemical composition and curvature.

14. The system of claim 9, wherein the data acquisition and control system determines a rate of absorption based on one or more of the parameters determined over one or more time intervals and wherein one or more of the characteristics of the porous substrate that are determined based at least in part on the rate of absorption.

15. The system of claim 1, wherein the delivery device, illumination source, imaging device and processor are in fixed positions relative to each other.

16. The system of claim 1, wherein the data acquisition and control system is configured to automatically initiate the delivery device to apply a sample to a substrate, to initiate the imaging device to acquire one or more images of the substrate in an area corresponding to the target point as the sample is absorbed by the substrate, and to identify and map the sample in the images.

17. The system of claim 16, wherein the data acquisition and control system is configured to identify one or more major and minor dimensions of the sample.

18. The system of claim 16, wherein the data acquisition and control system is configured to acquire one or more static measurements and one or more dynamic measurements of the sample.

19. The system of claim 18, wherein one or more of the static measurements comprise one or more of, major diameter, semi-major diameter, minor diameter, semi-minor diameter, spot edge regularity and total area.

20. The system of claim 18, wherein one or more of the dynamic measurements comprise one or more of, rate of absorption, changes in major and minor dimensions, color intensity, grey scale intensity and reflectance.

21. The system of claim 1, wherein the light source is a strobe light.

* * * * *